United States Patent
Yang (10) Patent No.: US 8,079,996 B2
(45) Date of Patent: Dec. 20, 2011

(54) CLOTH DIAPER THE SIZE OF WHICH IS ADJUSTABLE

(75) Inventor: Jason Yang, Taichung (TW)

(73) Assignee: 3RTW International Corporation, Taichung (TW)

( * ) Notice: Subject to any disclaimer, the term of this patent is extended or adjusted under 35 U.S.C. 154(b) by 210 days.

(21) Appl. No.: 12/367,587

(22) Filed: Feb. 9, 2009

(65) Prior Publication Data

US 2010/0204668 A1 Aug. 12, 2010

(51) Int. Cl.
*A61F 13/15* (2006.01)
*A61F 13/20* (2006.01)
(52) U.S. Cl. ......... 604/392; 604/386; 604/389; 604/391
(58) Field of Classification Search .................. 604/386, 604/378, 391, 389, 392
See application file for complete search history.

(56) References Cited

U.S. PATENT DOCUMENTS

| 4,798,603 | A  | * | 1/1989 | Meyer et al. | 604/378 |
| 5,383,872 | A  | * | 1/1995 | Roessler et al. | 604/391 |
| 2003/0097105 | A1 | * | 5/2003 | Chen et al. | 604/378 |
| 2007/0156111 | A1 | * | 7/2007 | Dalal et al. | 604/389 |
| 2009/0029616 | A1 | * | 1/2009 | Kanatani | 442/189 |

* cited by examiner

*Primary Examiner* — Melanie Hand
(74) *Attorney, Agent, or Firm* — Ming Chow; Sinorica, LLC (57) ABSTRACT

A cloth diaper the size of which is adjustable is mainly made up with a surface layer cloth and a liner layer cloth and is provided with a waistline section. The cloth diaper further includes an adjusting unit provided with two buckling parts, and an adjusting surface opposite to the buckling parts. Thus, to adjust the cloth diaper to a determined size, only each of the buckling parts of the adjusting unit is buckled and fixed onto the adjusting surface to form a cloth diaper the size of which is properly adjustable. Thus, following the child and infant's figure, the cloth diaper may be adjusted randomly.

4 Claims, 8 Drawing Sheets

CLOTH DIAPER THE SIZE OF WHICH IS ADJUSTABLE

BACKGROUND OF THE INVENTION

1. Field of the Invention

This invention relates to a cloth diaper the size of which is adjustable.

2. Description of the Related Art

Figure 1:
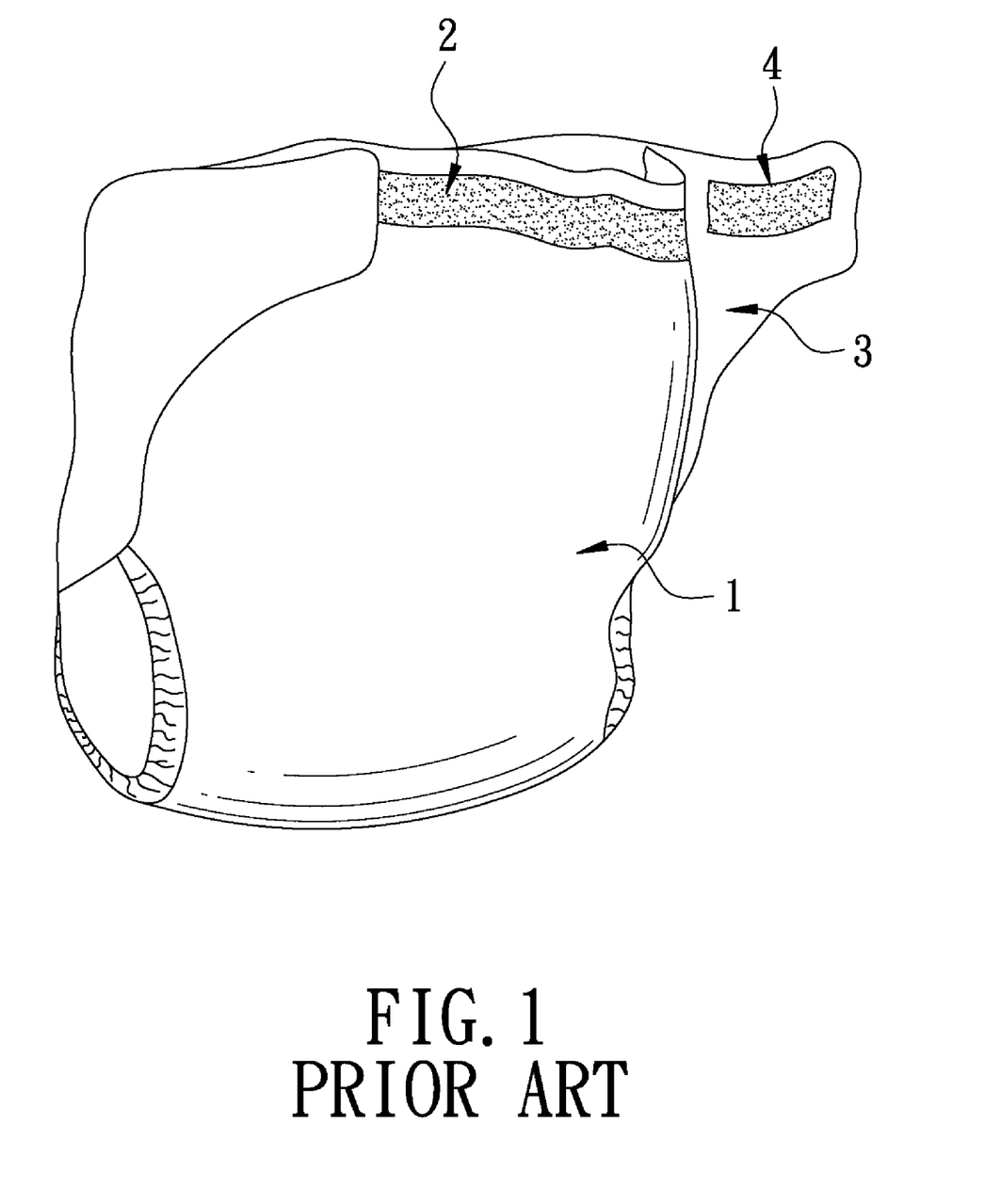
FIG. 1 is a 3D view of a conventional cloth diaper that is adjusted for waistline by means of a velcro strap.

Refer to FIG. 1 show as a 3D view illustrating a conventional cloth diaper, a female velcro strap and a male one of which are used to adjust the waistline. The conventional diaper comprises a surface layer cloth 1 and a liner layer cloth 3. The surface layer cloth 1 is provided with a lengthwise female velcro strap 2. The female velcro strap 2 is provided at one side of the top mouth of cloth diaper. The liner layer cloth 3 one side of which is formed with a male velcro strap 4 is opposite to the female velcro strap 2. Further, the female velcro strap 2 ties with the liner layer cloth 3. Although the size of cloth diaper may be adjusted for the waistline by means of the female velcro strap 2 and the male velcro strap 4, the waistline is limited to the length of the female velcro strap 2. Further, for example, when a medium- or large-sized diaper is used for a small child or infant, although the diaper may be adjusted for the waistline, the diaper cannot be adjusted for height, thereby the diaper being too large or wrapping up to the chest.

Figure 2:
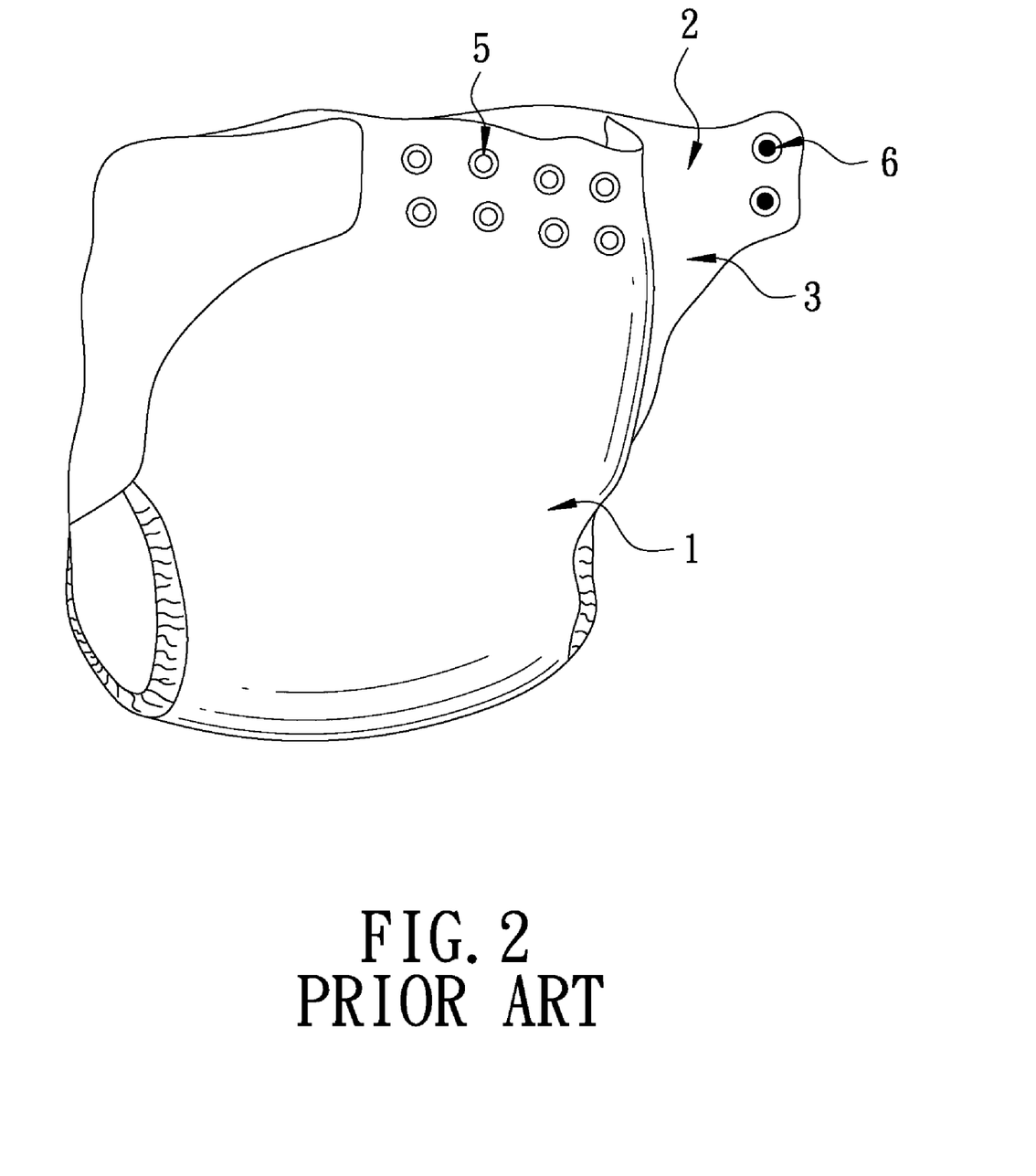
FIG. 2 is a 3D view of a conventional cloth diaper that is adjusted for waistline by means of a button.

Refer to FIG. 2 show as a 3D view illustrating the conventional cloth diaper, buttons of which are used to adjust the waistline. In another manner of adjusting the cloth for waistline, the surface layer cloth 1 is provided with several female buttons 5. The buttons 5 are provided at one side of the top mouth of cloth diaper. One side of the liner layer cloth 2 is formed with a male button 6 is opposite to the female button 5. The female button 5 is buckled with the male button 6. Although the size of cloth diaper may be adjusted for the waistline by means of the female buttons 5 and the male buttons 6, adjustment may be made for waistline but height by means of the female buttons 5 only spaced in the distance of intervals.

The conventional diaper cannot be properly adjusted for the child or infant's waistline and height. Thus, improvement is necessarily made.

Consequently, because of the technical defects of described above, the applicant keeps on carving unflaggingly through wholehearted experience and research to develop the present invention, which can effectively improve the defects described above.

SUMMARY OF THE INVENTION

A cloth diaper the size of which is adjustable according to this invention is mainly made up with a surface layer cloth and a liner layer cloth and is provided with a waistline section. The cloth diaper further comprises an adjusting unit provided with two buckling parts, and an adjusting surface opposite to the buckling parts. Thus, to adjust the cloth diaper to a determined size, only each of the buckling parts of the adjusting unit is buckled and fixed onto the adjusting surface to form a cloth diaper the size of which is properly adjustable.

Thus, following the child and infant's figure, the cloth diaper may be adjusted randomly.

DETAILED DESCRIPTION OF THE PREFERRED EMBODIMENTS

Now, the present invention will be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 3:
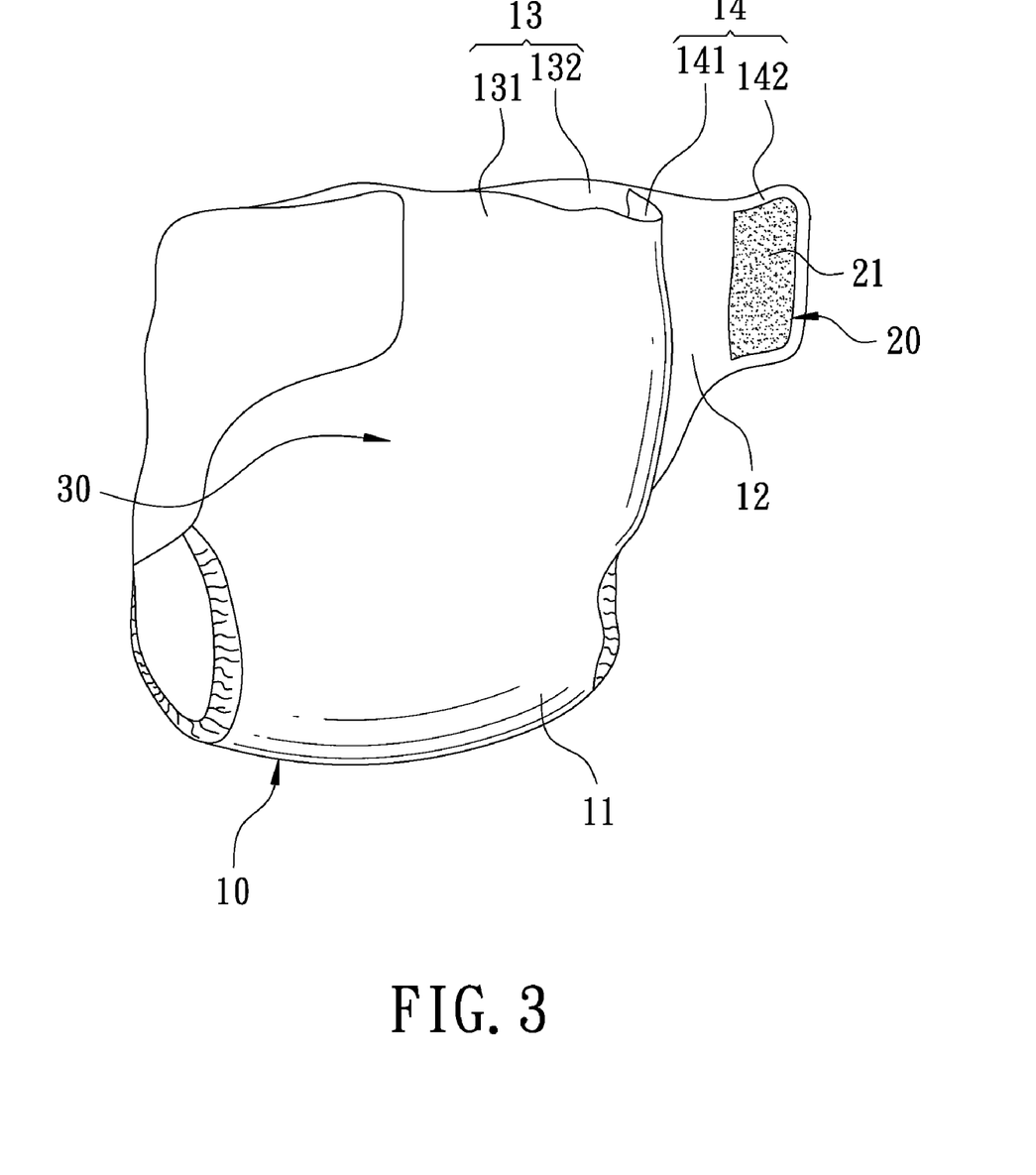
FIG. 3 is a 3D view of a preferred embodiment of this invention.

Firstly, with reference to FIG. 3 shown as a 3D view of a preferred embodiment of this invention, a cloth diaper further comprises a cloth 10, an adjusting unit 20, an adjusting surface 30, an absorbent pad 40, and a waterproof stuff 50.

The cloth 10 is made up with a surface layer cloth 11 and a liner layer cloth 12. In the preferred embodiment of this invention, the cloth 10 is made of looped knit fabric and is formed with a waistline section 13. The waistline section 13 is further divided into a front waistline section 131 and a rear waistline section 132. Also, a wing portion 14 extends from the two sides of the waistline section 13, and further where the wing portion 14 is formed, a front waistline wing portion 141 and a rear waistline wing portion 142 are separately formed.

Figure 4:
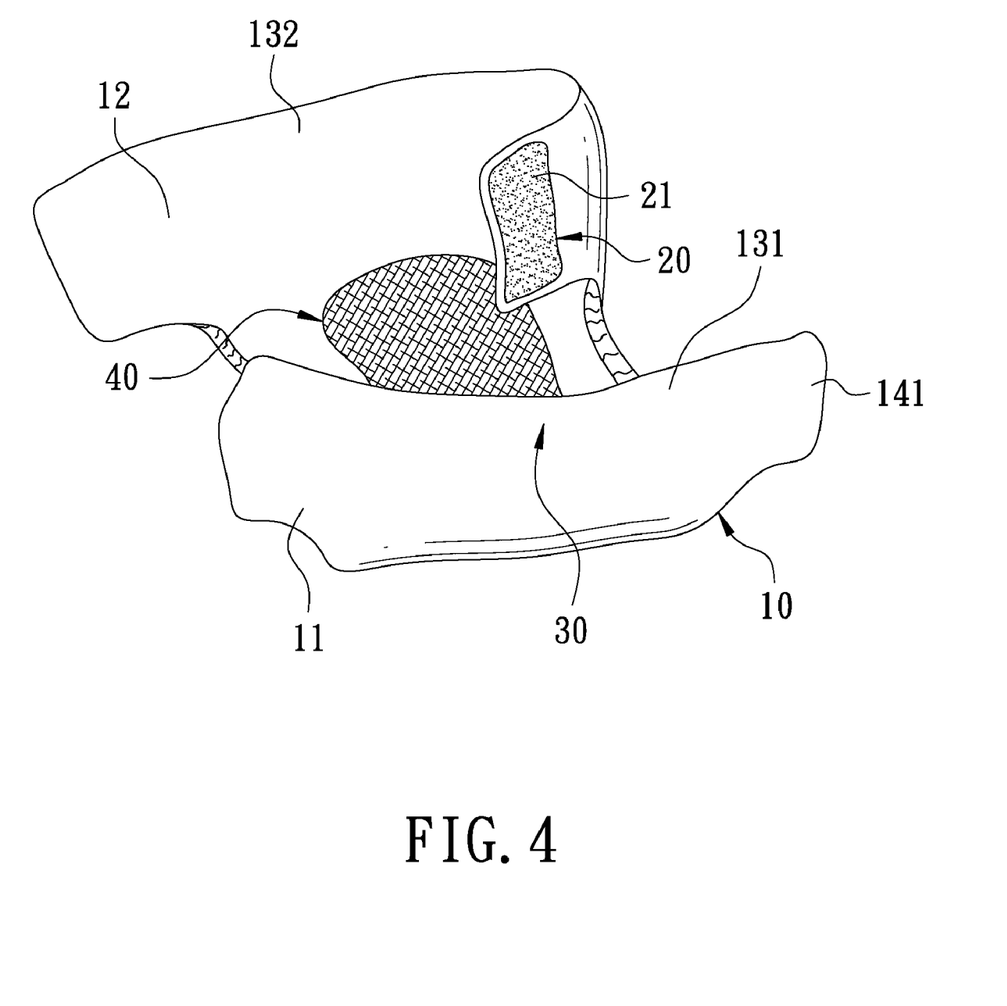
FIG. 4 is a 3D view of another preferred embodiment of this invention.

The adjusting unit 20 is mainly provided with two buckling parts 21. The buckling parts 21 are provided separately on the wing portion 14 of waistline section 13 and are featured with adjustment for fixing. In the preferred embodiment of this invention, the fixed buckling side of the buckling part 21 is formed with several hook-shaped parts. The buckling parts 21 of the adjusting unit 20 are separately arranged in the liner layer cloth 12 of rear waistline wing portion 142. With reference to FIG. 4 shown as a 3D view of the other embodiment of this invention, the buckling parts 21 of the adjusting unit 20 may be also arranged in the surface layer cloth 11 of the rear waistline wing portion 142.

The adjusting surface 30 is formed at a site opposite to the buckling parts 21 of adjusting unit 20, thereby the buckling parts 21 being used for adjustment and fixing. The adjusting surface 30 is made of a looped knit fabric cloth.

Figure 5:
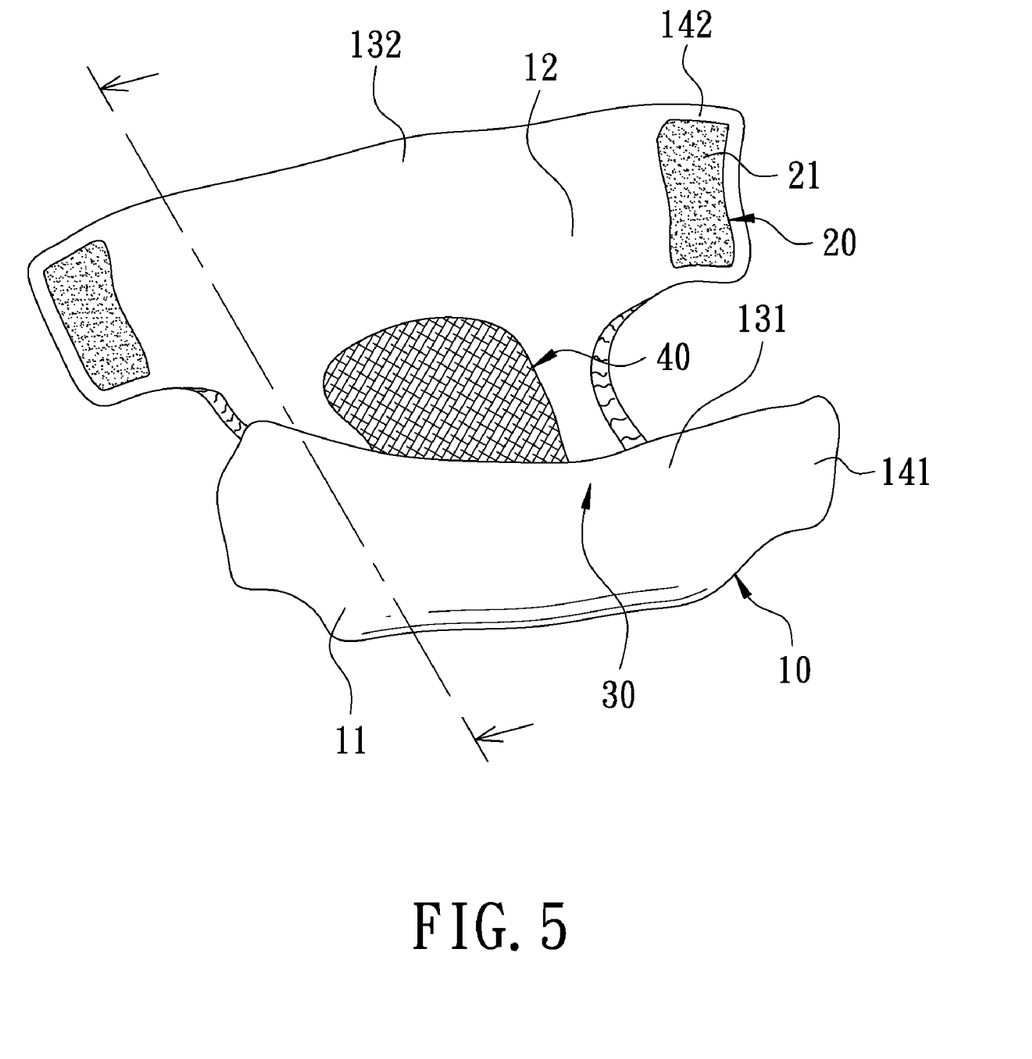
FIG. 5 is a 3D view of an absorbent pad according to this invention that is provided on the inner surface of a liner layer cloth.

With reference to FIG. 5, the absorbent pad 40 is formed on the surface of liner layer cloth 12 oppositely contacting the body of child, and is made of cotton for enhancement of absorbency. In the preferred embodiment, the absorbent pad 40 may be stick or sewn to fix onto the surface of liner layer cloth 12.

Figure 6:
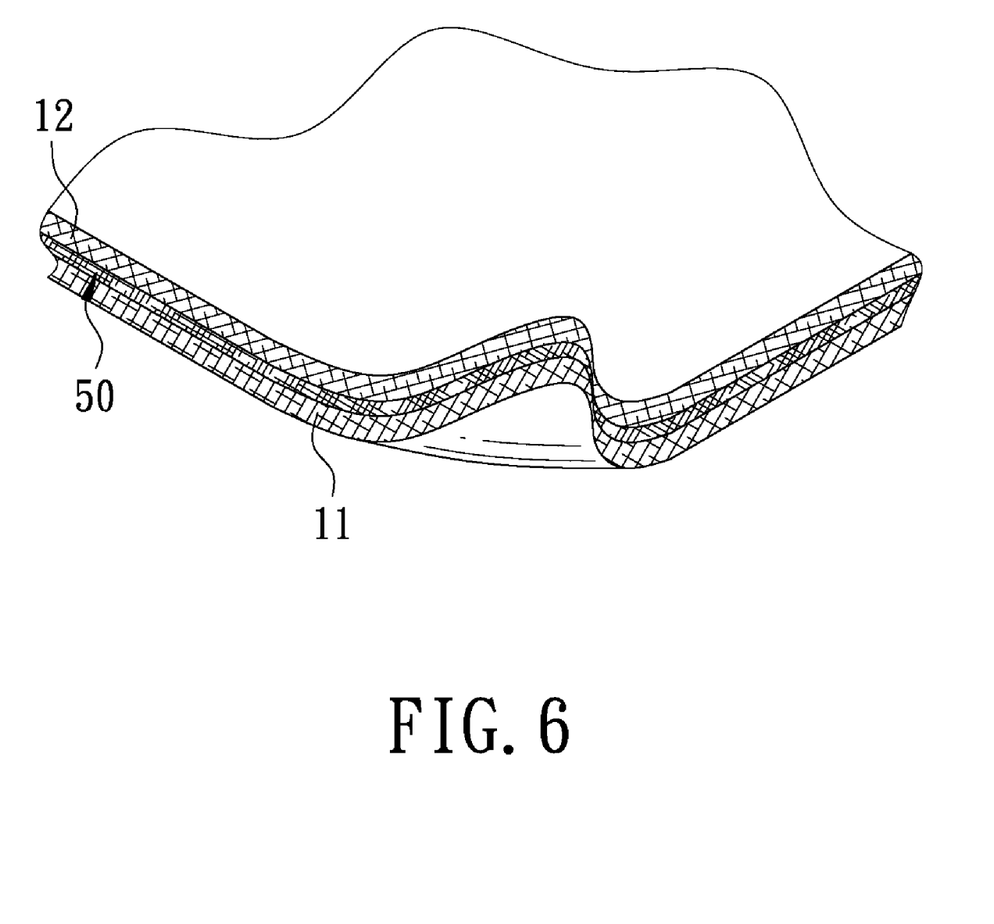
FIG. 6 is a partial sectional view of FIG. 5, illustrating a waterproof stuff provided between the liner layer cloth and a surface layer cloth.

With reference to FIG. 6, the waterproof stuff 50 is provided between the surface layer cloth 11 and the liner layer cloth 12 for enhancement of the capability of waterproof of the cloth diaper. In the preferred embodiment of this invention, the waterproof stuff 50 is a thin film and may be made from polypropylene (PP), polyethylene (PE), polytetrafluoroethylene (PTFE), or polyurethane (PU).

With further reference to FIG. 3 shown as a 3D view illustrating the preferred embodiment of this invention, to securely buckle the cloth diaper, only the buckling parts 21 provided in the liner layer cloth 12 of the rear waistline wing portion 142 are buckled and fixed onto the adjusting surface 30 to make the cloth diaper more fit the children and the infants.

Figure 7:
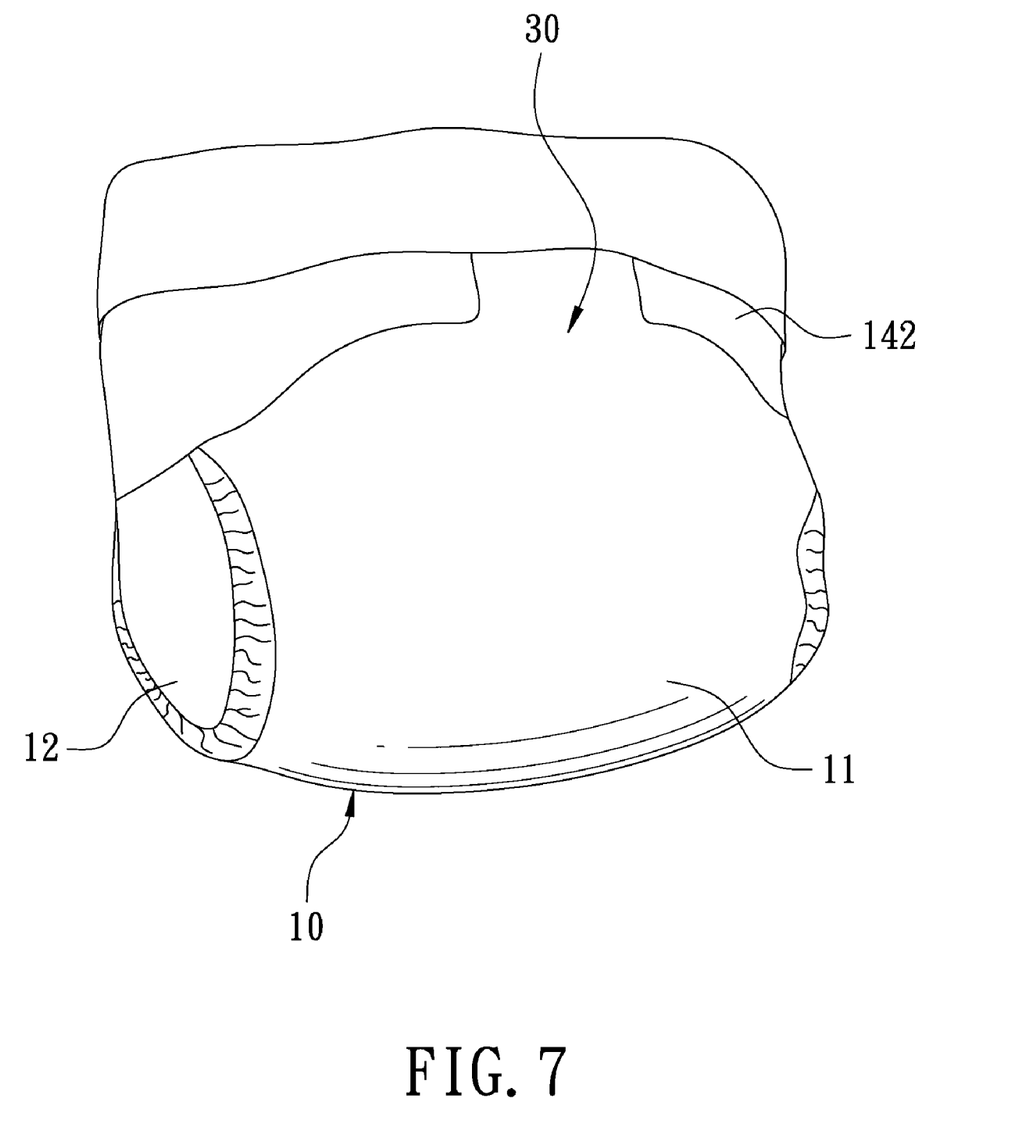
FIG. 7 is a schematic view illustrating a service state of this invention.

With reference to FIG. 7 shown as a schematic view illustrating a service state of this invention, when a smaller child or infant wears the cloth diaper, only the buckling parts 21 at two sides are buckled into a lower site of the adjusting surface 30; further, the cloth diaper opposite to the child's waistline is turned and folded down properly in length so as not to wrap around the child or infant's chest and not to affect the comfort index of wear of the cloth diaper. The adjusting surface 30 of cloth diaper ranges to the outer surface of surface layer cloth 11 or the surface of liner layer cloth 12 contacting the child's body, so the range of buckling of the buckling part 21 is widened. Besides, on the surface layer cloth 11 and liner layer cloth 12 of the cloth diaper, the adjusting surface 30 is just designed into that made of looped knit fabric cloth; a portion except the adjusting surface 30 may be optionally made of another cloth to form the surface layer cloth 11 or the liner layer cloth 12 for achievement of the effect of fix.

Figure 8:
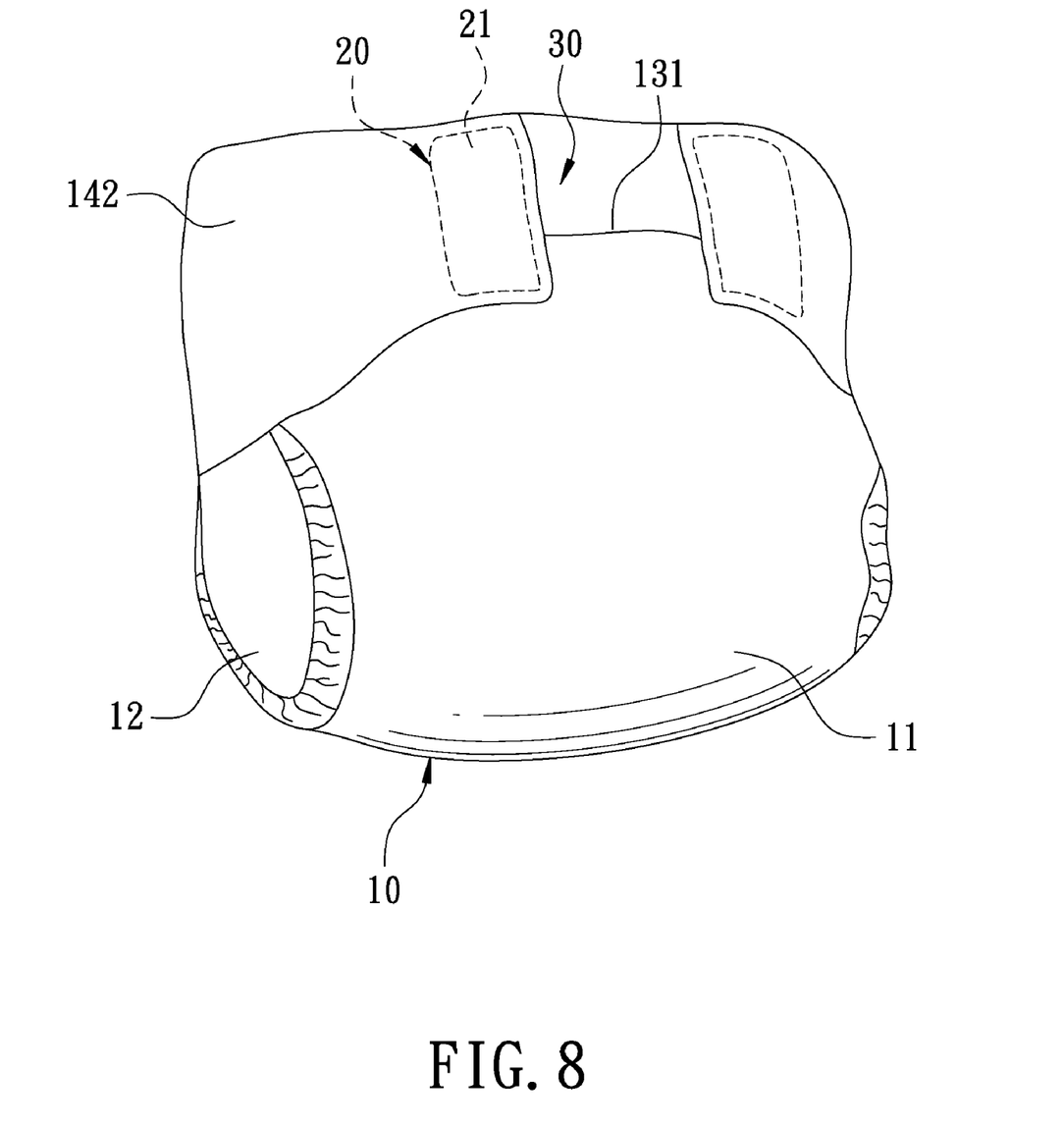
FIG. 8 is a schematic view illustrating the other service state of this invention.

With reference to FIG. 8 shown as a schematic view illustrating the other service state of this invention, the front waistline section 131 of the cloth diaper may also firstly be turned outwards and folded to make the surface of liner layer cloth 12 that contacts the child's body form the adjusting surface 30. The adjusting surface 30 is buckled with and fixed to the buckling part 21 provided in the liner layer cloth 12 of rear waistline wing portion 142 so as not to wrap around the child or infant's chest and not to affect the comfort index of wear of the cloth diaper. Next, an absorbent cloth is provided between the surface layer cloth 11 and the liner layer cloth 12 for displacement of the waterproof cloth 50. The absorbent cloth may be made of non-woven fabric or cotton for enhancement of absorbency. Further, the combination of the surface layer cloth 11, liner layer cloth 12, and absorbent cloth is a conventional art apparent to those who are skilled, so unnecessary details are not given here. Next, the adjusting unit 20 of cloth diaper is buckled with and fixed to the adjusting surface 30 in the same manner for achievement of the same effect of buckling.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A cloth diaper with adjustable sizes comprises,
a surface layer cloth;
a liner layer cloth;
a waistline section;
an adjusting unit with at least two buckling parts;
the two buckling parts being separately arranged at wing portions;
the wing portions being formed at two sides of the waistline section;
an adjusting surface being formed at a site opposite to the buckling parts of the adjusting unit, thereby the buckling parts being used for adjustment and fixing;
the liner layer cloth of cloth diaper being made of looped knit fabric;
the waistline section of cloth diaper being formed with a front waistline section and a rear waistline section and separately with a front waistline wing and a rear waistline wing, in which the buckling parts of the adjusting unit are separately arranged in the liner layer cloth of rear waistline wing, wherein the front waistline section is forward turned and folded so as to make the adjusting surface formed on the liner layer cloth to be securely buckled with the buckling parts; and
a thin film waterproof stuff is further provided between the surface layer cloth and liner layer cloth of the cloth diaper for enhancement of the capability of waterproof.

2. The cloth diaper with adjustable sizes according to claim 1, wherein the buckling part opposite to the buckling side of the adjusting surface is formed with several hook-shaped parts and buckled with the adjusting surface.

3. The cloth diaper with adjustable sizes according to claim 1, wherein an absorbent pad is further provided on the liner layer cloth.

4. The cloth diaper with adjustable sizes according to claim 1, wherein an absorbent stuff is also provided between the surface layer cloth and liner layer cloth of the cloth diaper for enhancement of the absorbency.

\* \* \* \* \*